US010209221B2

(12) United States Patent
Davis

(10) Patent No.: US 10,209,221 B2
(45) Date of Patent: Feb. 19, 2019

(54) TESTING OF DRILL PIPE INSPECTION EQUIPMENT

(71) Applicant: Schlumberger Technology Corporation, Sugar Land, TX (US)

(72) Inventor: Corey J. Davis, Spring, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 284 days.

(21) Appl. No.: 14/734,100

(22) Filed: Jun. 9, 2015

(65) Prior Publication Data

US 2015/0361784 A1 Dec. 17, 2015

Related U.S. Application Data

(60) Provisional application No. 62/012,065, filed on Jun. 13, 2014.

(51) Int. Cl.
*G01N 27/82* (2006.01)
*G01R 31/02* (2006.01)
*G01R 31/00* (2006.01)

(52) U.S. Cl.
CPC .......... *G01N 27/82* (2013.01); *G01R 31/001* (2013.01); *G01R 31/021* (2013.01); *G01R 31/025* (2013.01)

(58) Field of Classification Search
CPC ........ G01N 24/08; G01N 24/81; G01N 24/82; G01N 24/84; G01N 24/10; G01V 3/08; G01V 3/81; G01V 3/10; G01V 3/101; G01V 3/104; G01V 3/105; G01V 3/18; G01V 3/26; G01V 3/28; G01V 3/20; G01V 3/22; G01V 3/24; G01V 3/265
See application file for complete search history.

(56) References Cited

U.S. PATENT DOCUMENTS

| 6,585,044 | B2* | 7/2003 | Rester ............ E21B 47/10 166/187 |
| 6,924,640 | B2* | 8/2005 | Fickert .......... E21B 47/082 324/220 |
| 6,950,034 | B2* | 9/2005 | Pacault ......... E21B 17/028 340/855.2 |
| 7,096,976 | B2* | 8/2006 | Paluch .......... E21B 21/10 166/250.17 |
| 7,293,461 | B1 | 11/2007 | Girndt |

(Continued)

OTHER PUBLICATIONS

Drilco, "Inspection Services—Inspection and maintenance at the rig or in the shop," 2013, 4 pages.

*Primary Examiner* — Tung X Nguyen
*Assistant Examiner* — Dominic Hawkins

(57) ABSTRACT

An equipment testing apparatus may include one or more test connections. The equipment testing apparatus may also include a power cable and/or power supply in electrical communication with the one or more test connections. The power cable and/or power supply may be configured to provide electrical energy to the one or more test connections to verify the performance of various components of the equipment to be tested. In particular, an equipment testing apparatus may be configured to verify the performance of various components of drill pipe inspection equipment. Components of drill pipe inspection equipment that are tested may include a drive motor, an electromagnetic coil, and a signal cable.

19 Claims, 8 Drawing Sheets

(56) References Cited

U.S. PATENT DOCUMENTS

| | | | | |
|---|---|---|---|---|
| 7,519,886 B2* | 4/2009 | Tsao | ............... | G01B 31/318555 |
| | | | | 365/201 |
| 8,072,347 B2* | 12/2011 | Santoso | ............... | E21B 17/028 |
| | | | | 324/221 |
| 8,640,558 B2* | 2/2014 | Cabuz | ................... | G01N 21/88 |
| | | | | 73/865.8 |
| 9,134,261 B2* | 9/2015 | Yoshikawa | ........ | G01N 23/2204 |
| 9,273,550 B2* | 3/2016 | Clark | .................... | E21B 47/122 |
| 2002/0069704 A1* | 6/2002 | Robb | .................. | G01N 27/902 |
| | | | | 73/622 |
| 2002/0177954 A1* | 11/2002 | Vail, III | .................. | G01V 3/24 |
| | | | | 702/7 |
| 2005/0087368 A1* | 4/2005 | Boyle | .................. | E21B 17/023 |
| | | | | 175/57 |
| 2008/0054150 A1* | 3/2008 | Stuby | .................. | B60N 2/0232 |
| | | | | 248/371 |
| 2008/0158005 A1* | 7/2008 | Santoso | ............... | E21B 17/028 |
| | | | | 340/854.4 |
| 2009/0038849 A1* | 2/2009 | Braden | ................ | E21B 17/028 |
| | | | | 175/40 |
| 2012/0007617 A1* | 1/2012 | Fisseler | .................. | G01N 17/02 |
| | | | | 324/700 |
| 2012/0268153 A1* | 10/2012 | Nickel | ............... | G01R 31/3025 |
| | | | | 324/754.31 |
| 2013/0015870 A1* | 1/2013 | Nickel | ............... | G01R 1/06772 |
| | | | | 324/754.03 |
| 2014/0062715 A1* | 3/2014 | Clark | .................... | E21B 47/122 |
| | | | | 340/853.2 |
| 2014/0224481 A1* | 8/2014 | Scheibelmasser | .... | E21B 47/122 |
| | | | | 166/250.01 |

* cited by examiner

TESTING OF DRILL PIPE INSPECTION EQUIPMENT

CROSS-REFERENCE TO RELATED APPLICATIONS

This application claims the benefit of, and priority to, U.S. Patent Application Ser. No. 62/012,065, filed Jun. 13, 2014, which application is expressly incorporated herein by this reference in its entirety.

BACKGROUND INFORMATION

Drill pipes and tubulars are inspected using an inspection unit 100 that includes an electromagnetic coil 102 that moves with a driving device (also known as a buggy) 104, as shown in FIG. 1. The buggy 104 includes a motor 106 that drives a drive wheel 108. The inspection unit 100 also includes a detection head 110 used to detect faults in a drill pipe or tubular 112. The motor 106 drives the inspection unit 100 along a length of the drill pipe or tubular 112 while collecting information regarding various aspects of the drill pipe or tubular 112.

As the inspection unit 200 moves along the length of the drill pipe or tubular 212 as shown in FIG. 2, the detection head 210 performs electromagnetic interference ("EMI") or other testing. The inspection unit 200 may collect information regarding the structural integrity of the drill pipe or tubular 212, such as material composition, material thickness, corrosion, deformation, or other aspects of the drill pipe or tubular 212.

The inspection unit 300 communicates with an EMI Console 314 as shown in FIG. 3, by using an inspection unit cable 316. The EMI Console 314 is in communication with a computer 318. Different inspection unit cables 316 allow the EMI Console 314 to provide electrical energy and operational commands to the inspection unit 300 and to receive data from the inspection unit 300. The EMI Console 314 communicates with the computer 318 through an EMI Console cable 320 to interpret the data.

Faults can develop during operation of the inspection unit 300. Certain faults in the inspection unit 300, such as a short circuit, result in damage to the EMI Console 314 upon connection to a faulty inspection unit 300.

SUMMARY

In some embodiments, an equipment testing apparatus includes a test connection including a first input and a first output. The first test connection is also in electrical communication with a power cable. The power cable is configured to couple to an electrical energy source.

In some embodiments, an equipment testing apparatus includes a first test connection, a second test connection, and a third test connection. A power cable is configured to couple to an electrical energy source and provide electrical energy to the first, second, and third test connections.

In some embodiments, an equipment testing apparatus includes an input and an output with a fault indicator array in electrical communication between the input and the output. The fault indicator array is configured to identify a faulty electrical connection.

In some embodiments, a method testing inspection equipment includes providing an equipment testing apparatus and coupling a first test connection of the equipment testing apparatus to a motor. Electrical energy is provided to the motor and the performance of the motor is verified.

In some embodiments, a system for testing inspection equipment includes an equipment testing apparatus and a motor. The motor is coupled to a first test connection of the equipment testing apparatus. The first test connection is in electrical communication with the motor.

In some embodiments, a testing apparatus for drill pipe inspection equipment includes a first test connector, a second test connector, and a fault indicator configured to indicate an operational condition of drill pipe inspection equipment coupled to the first and second test connectors.

In some embodiments, a method for testing drill pipe inspection equipment may include accessing drill pipe inspection equipment that includes at least three test connections that selectively allow electrical communication therethrough. A motor may be coupled to the first test connection and electrical communication can be selectively allowed to test motor direction. An electromagnetic coil can be coupled to the second test connection and electrical communication can be selectively allowed to test an electromagnetic field of the electromagnetic coil. A signal cable can be coupled to the third test connection and electrical communication can be selectively allowed to test a condition of multiple wires inside the signal cable.

In another embodiment, a method for testing drill pipe inspection equipment includes coupling a cable of drill pipe inspection to a testing apparatus. Electrical energy is provided to the cable, and performance of the cable is verified.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION

Some embodiments of the present disclosure relate to inspection services. More particularly, some embodiments may relate to devices for testing operation of equipment used in performing inspection services. More particularly still, some embodiments may relate to methods and devices for testing inspection equipment at a wellsite. Further, some embodiments may relate to testing cables of inspection equipment using portable equipment.

Figure 1:
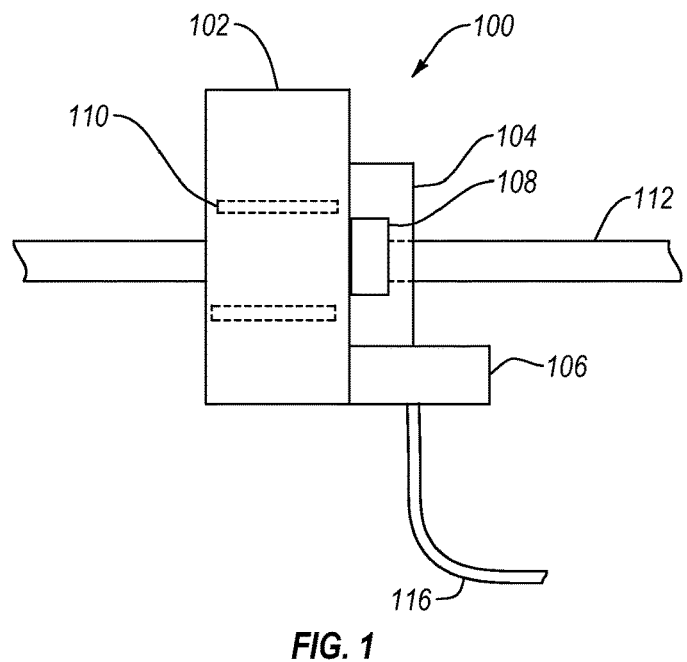
FIG. 1 is a side view of an inspection unit according to one or more embodiments disclosed herein.
Figure 2:
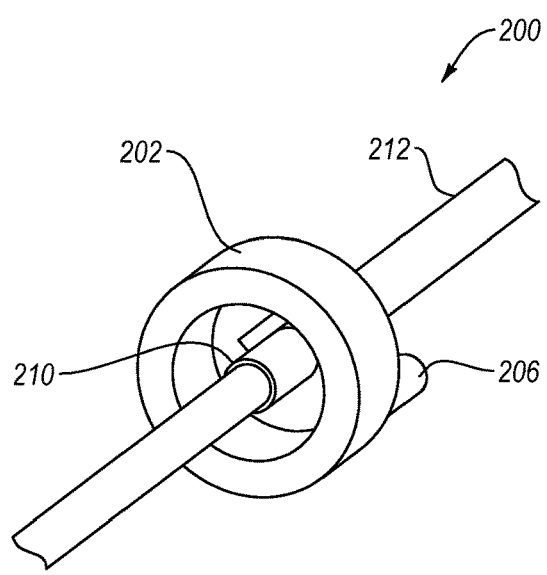
FIG. 2 is a perspective view of an inspection unit according to one or more embodiments disclosed herein.
Figure 4:
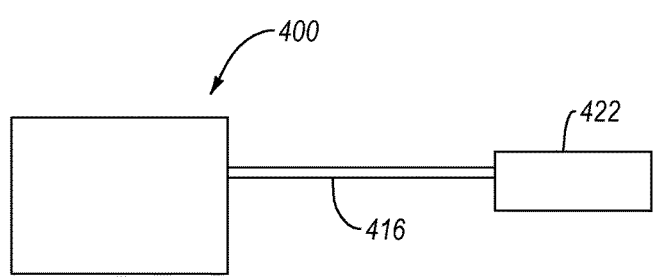
FIG. 4 is a schematic view of an equipment testing system according to one or more embodiments disclosed herein.

FIGS. 4 through 13 depict various embodiments of a testing device, according to one or more embodiments of the present disclosure. In particular, FIG. 4 depicts a testing apparatus 422 coupled to an inspection unit 400. The testing apparatus 422 may be coupled to the inspection unit 400 by an inspection unit cable 416. The inspection unit cable 416 may be: a motor cable providing electrical communication with a motor, such as that depicted in FIGS. 1 and 2; an electromagnetic coil cable providing electrical communication with an electromagnetic coil, such as that depicted in FIGS. 1 and 2; an electromagnetic coil cable providing data communication with a detection head, such as that depicted in FIGS. 1 and 2; or other cable providing communication with components of the inspection unit 400. The inspection unit cable 416 may be flexible; however, the inspection unit cable 416 may be rigid or partially rigid in some embodiments. The inspection unit cable 416 may include connectors at ends thereof to couple the inspection unit cable 416 to the testing apparatus 422 and the inspection unit 400, respectively.

Figure 5:
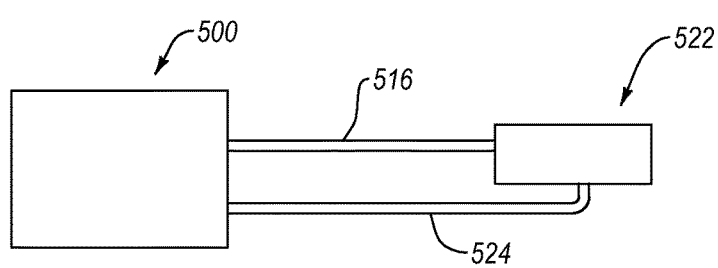
FIG. 5 is a schematic view of an equipment testing system testing multiple components of an inspection unit simultaneously according to one or more embodiments disclosed herein.

FIG. 5 depicts another embodiment of a testing apparatus 522 coupled to an inspection unit 500 by a plurality of inspection unit cables. The testing apparatus 522 may couple to the inspection unit 500 by a first inspection unit cable 516 and a second inspection unit cable 524 to allow the testing of a plurality of components in sequence or simultaneously. For example, the first inspection unit cable 516 may be a motor cable and may allow testing of a motor of inspection unit 500, while the second inspection unit cable 524 may be an electromagnetic coil cable and may allow testing of an electromagnetic coil of inspection unit 500.

Figure 6:
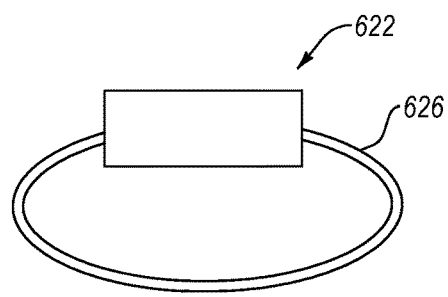
FIG. 6 is a schematic view of an equipment testing system testing an electrical cable according to one or more embodiments disclosed herein.

FIG. 6 depicts a testing apparatus 622 with at least two connectors allowing integrity testing of an electrical cable, such as signal cable 626. The signal cable 626 may be coupled to the testing apparatus 622 at both ends in some embodiments. The testing apparatus 622 may then apply an input current and/or voltage to the signal cable 626 to evaluate the integrity of the signal cable 626. The testing apparatus 622 may compare the input current and/or voltage to an output current and/or voltage. The testing apparatus 622 may determine whether the signal cable 626 has a fault along the length of the signal cable. The signal cable 626 may include a plurality of electrical wires. The testing apparatus 622 may also determine whether the signal cable 626 has a fault along the length of one of the wires within the signal cable 626, and potentially which wires have such a fault.

Figure 7:
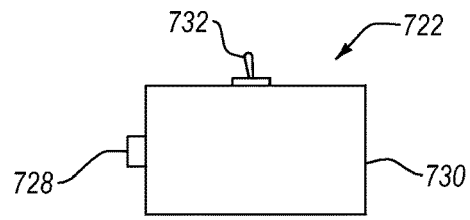
FIG. 7 depicts an equipment testing apparatus having a test connection according to one or more embodiments disclosed herein.

FIG. 7 is a schematic representation of a testing apparatus 722 including a test connection 728 mounted to a housing 730. The housing 730 may also include a switch 732. The test connection 728 may be configured to receive an inspection unit cable (not shown). The test connection 728 may include multiple connectors, which may also operate as an input and an output. The testing apparatus 722 may provide electrical energy to the test connection 728 such that a coupled inspection unit cable may receive electrical energy. The switch 732 may be in electrical communication with the input and/or the output such that the switch 732 may selectively allow electrical communication between the input and output of the test connection 728. The switch 732 may be any suitable type of switch to selectively allow electrical communication between the input and output of the test connection 728. For example, the switch 732 may include a two-position gate switch or toggle switch that either allows electrical communication to the input of the test connection 728 ("closed position") or prevents electrical communication to the input of the test connection 728 ("open position"). In another example, the switch 732 may include a three-position reverse switch. The three-position reverse switch may include a first position that allows electrical communication (e.g., to the input or between the input and output of the test connection 728 ("closed position")), a second position that restricts or prevents electrical communication ("open position"), and a third position that allows electrical communication with an opposite polarity to the first position ("reverse position"). In at least one embodiment, a three-position reverse switch may allow for testing a motor in both a forward and reverse operating direction.

Figure 8:
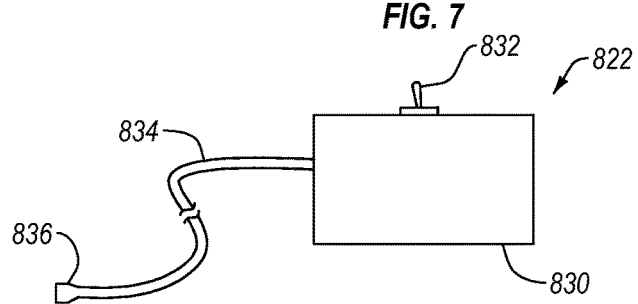
FIG. 8 depicts an equipment testing apparatus having a test cable according to one or more embodiments disclosed herein.

FIG. 8 is a schematic representation of a testing apparatus 822 including a test cable 834 mounted to a housing 830. The test cable 834 may be affixed to the housing 830 and include a test cable connection 836. The test cable connection 836 may be similar to the test connection 728 depicted in FIG. 7. The test cable connection 836 may be configured to couple directly or indirectly to an inspection unit (not shown). For example, an inspection unit cable may include a male connection at both ends of the inspection unit cable. The test connection 728 depicted in FIG. 7 may include a female connection to couple to the inspection unit cable. The test cable connection 836, however, may have a male connection to couple to the inspection unit without the use of an inspection unit cable. In at least one embodiment, a test cable 834 may allow for testing of an inspection unit independently of the inspection unit cables. In at least one embodiment, testing of the inspection unit independently of the inspection unit cables may allow for greater isolation of variables during testing.

Figure 9:
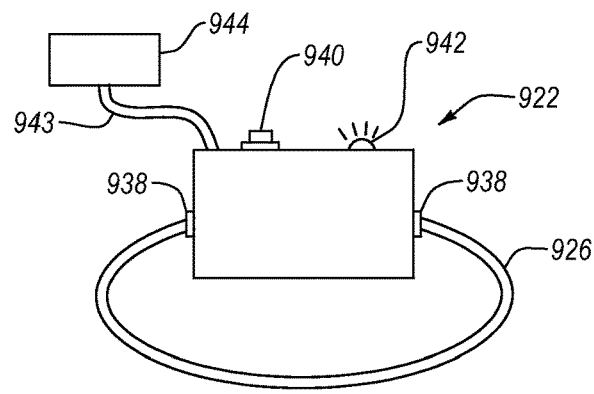
FIG. 9 is a schematic view of an equipment testing system having a power supply and a fault indicator testing an electrical cable according to one or more embodiments disclosed herein.

FIG. 9 depicts a testing apparatus 922 configured to test a signal cable 926. A testing apparatus 922 may include a test connection with a pair of connectors 938 configured to couple to each end of the signal cable 926. The testing apparatus 922 may also include a switch 940 configured to selectively allow electrical communication between the pair of connectors 938. The switch 940 may be a switch similar to the switch 732 described in relation to FIG. 7. The switch 940 may also be a pressure-activated switch such as a button or a spring-loaded toggle. The switch 940 may allow electrical communication between the test connectors 938 (e.g., to one test connector 938, through a coupled signal cable 926, and to the second test connector 938) when a force is applied to depress the switch 940 into a closed position. The switch 940 may restrict or prevent electrical communication between the test connectors 938 when a force is not applied to the switch 940 and it remains in an open position. The switch 940 may allow electrical communication between the test connectors 938 in coordination with electrical communication between the test connectors 938 provided by a "good" signal cable 926.

The testing apparatus 922 may include a fault indicator 942 that indicates to a user if the signal cable 926 contains a fault within. For example, a fault indicator 942 may include a light that illuminates when a circuit is completed. The circuit may include the switch 940 in a closed position and a signal cable 926 coupling the test connectors 938 to one another. A closed switch 940 and a signal cable 926 may provide electrical communication with the fault indicator 942. If the signal cable 926 contains a fault therein, such as a broken wire, the signal cable 926 may not provide electrical communication and the fault indicator 942 may not illuminate. In other embodiments, the fault indicator 942 may illuminate, but may change color (e.g., change from green to red). In still other embodiments, the fault indicator may include a light or other indicator that illuminates when the signal cable 926 has a fault, and does not illuminate when the circuit is closed (i.e., the signal cable is in good condition).

The testing apparatus 922 may include a power cable 943 configured to provide electrical energy from a power supply 944 to the testing apparatus 922. The power supply 944 may be an internal power supply, for example a battery pack, or an external power supply. For example, an external power supply may include a generator, a battery pack, a connection to a distributed power grid, a photovoltaic device, fuel cells, or other suitable power source.

Figure 10:
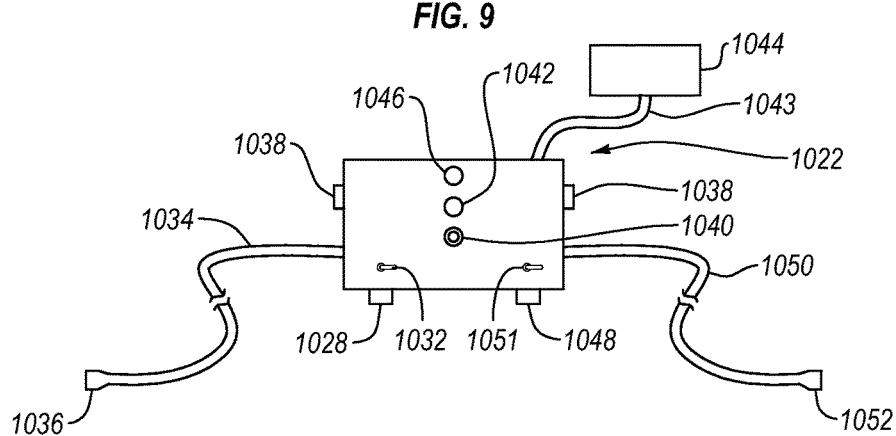
FIG. 10 is a top view of an equipment testing apparatus according to one or more embodiments disclosed herein.

FIG. 10 depicts a testing apparatus 1022 that includes a six test connectors for at least three test connections. When a power supply 1044 is coupled to the testing apparatus by the power cable 1043, a power indicator 1046 may illuminate. A first test connection may include a first connector 1028 and/or a second connector 1036. The first connector 1028 may couple to a first component of an inspection unit to be tested, and the second connector 1036 may also couple to the first component of the inspection unit (e.g., via a first test cable 1034). In some embodiments, the first and second connectors 1028, 2036 of the first test connection may couple to a motor (not shown) to be tested. A second test connection may include a third connector 1048 and/or a fourth connector 1052. The third connector 1048 may couple to a second component of an inspection unit to be tested, and the fourth connector 1052 may also couple to the second component of the inspection unit (e.g., via a second test cable 1050). In some embodiments, the third and fourth connectors 1048, 1052 of the second test connection may couple to an electromagnetic coil (not shown) to be tested. One or more third test connections may also be included for testing of components of an inspection unit to be tested. For example, a third test connection may include fifth and sixth connectors 1038. In some embodiments, the fifth and sixth test connectors may couple to a signal cable to be tested.

Electrical communication of the electrical energy with the first connector 1028 and/or the second connector 1036 may be selected using the first switch 1032 (e.g., to provide power to a motor). Electrical communication of the electrical energy with the third connector 1048 and/or the fourth connector 1052 may be selected using the second switch 1051 (e.g., to provide power to an electromagnetic coil). Electrical communication of the electrical energy with the fifth and sixth connectors 1038 may be selected using the third switch 1040 (e.g., to run power through a signal cable). The format or configuration of any connectors 1028, 1036, 1038, 1048, 1052 may be the same or may vary from each other.

Figure 11:
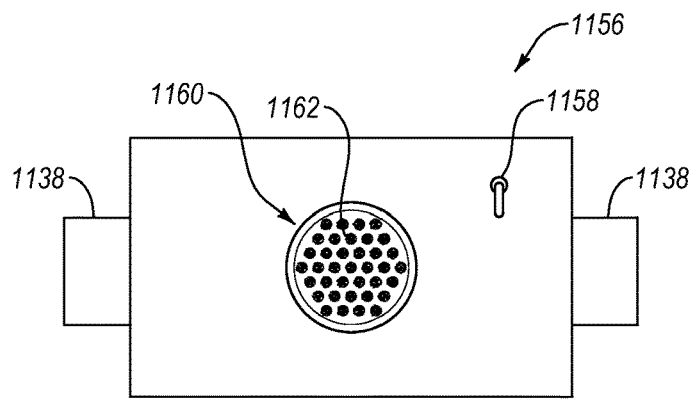
FIG. 11 depicts an electrical cable continuity testing apparatus according to one or more embodiments disclosed herein.
Figure 12:
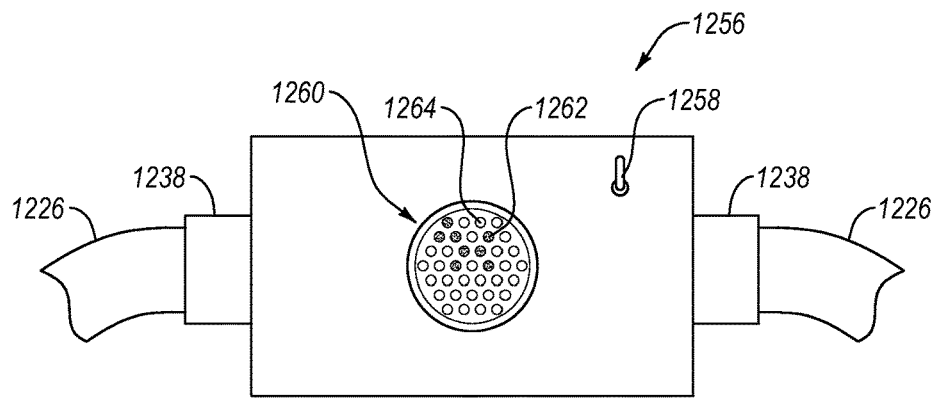
FIG. 12 depicts an electrical cable continuity testing apparatus in use according to one or more embodiments disclosed herein.

FIG. 11 depicts a signal cable continuity tester 1156 having test connections 1138 and a power switch 1158. The power switch 1158 may selectively allow electrical communication between the test connections 1138 and a fault indicator array 1160. The fault indicator array 1160 may include, for instance, a fault indicator 1162 for each wire in a signal cable 1226 (shown in FIG. 12). As shown in FIG. 12, the fault indicator array 1262 may visually indicate to a user which wires within the signal cable 1226 contain a fault. In some embodiments, indicating a fault may be done by illuminating a fault indicator 1264 for a "good" wire, while not illuminating the fault indicator 1262 when the wire contains a fault. In other embodiments, different colors of illumination may be used for one or more fault indicators to contrast a good wire with a faulty wire. In some embodiments, the fault indicator array 1260 may visually indicate to a user the faulty wires through a display correlating to the format of the test connection 1238 (e.g., the layout of fault indicators may generally match or correspond the layout of pins for a connector). For example, if the test connection 1238 with the signal cable 1226 has 28 active pins in a 32-pin connector, the fault indicator array 1260 may include a 36-location array including 28 fault indicators, such as light emitting diodes. In another embodiment, the fault indicator array 1260 may include a text readout that communicates to a user the pin location of a faulty wire. In another embodiment, the fault indicator array 1260 may include an arrangement of fault indicators 1262 dissimilar to the arrangement of pins in the test connection 1238. In at least one embodiment, the signal cable continuity tester 1256 may shorten the time necessary to identify a faulty wire within a signal cable 1226.

Figure 3:
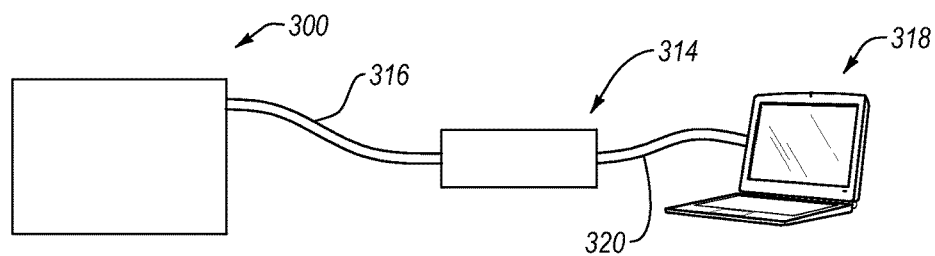
FIG. 3 is a schematic view of a control system of an inspection unit according to one or more embodiments disclosed herein.
Figure 13:
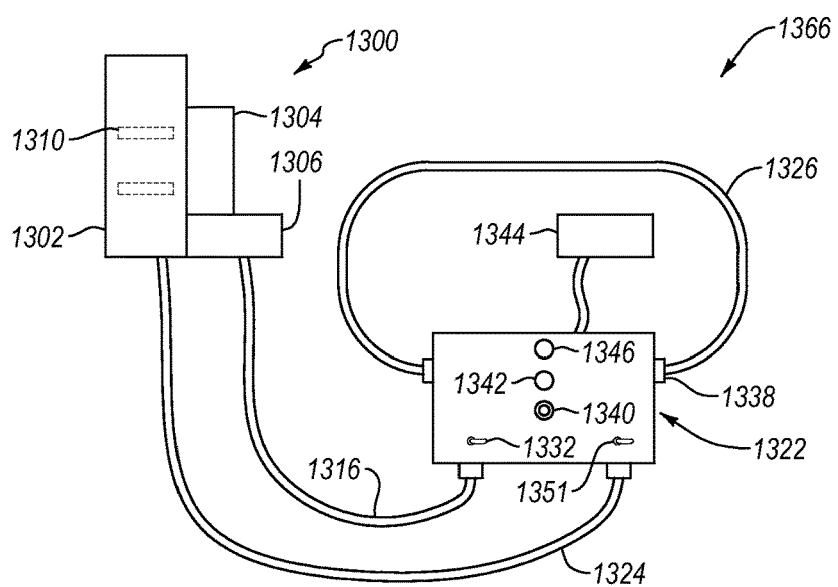
FIG. 13 depicts an inspection unit testing system according to one or more embodiments disclosed herein.

FIG. 13 depicts an equipment testing system 1366 including a testing apparatus 1322 configured to test various components of an inspection unit 1300. The testing apparatus 1322 may be similar to or the same as one or more of the embodiments described herein. In particular, the testing apparatus 1322 may be similar to or the same as the testing apparatus 1022 described in relation to FIG. 10. The testing apparatus 1322 may couple to a motor 1306 of a buggy 1304. The testing apparatus 1322 may couple to the motor 1306 via a first inspection unit cable 1316, which may be a motor cable, through a first test connection 1328. The testing apparatus 1322 may couple to an electromagnetic coil 1302. The testing apparatus 1322 may couple to the electromagnetic coil 1302 via a second inspection unit cable 1324, which may be an electromagnetic coil cable, through a second test connection 1348. The testing apparatus 1322 may couple to the signal cable 1326 through one or more third test connectors 1338. In some embodiments, the testing apparatus 1322 may be integrated into a computer and/or EMI console (i.e. 318 in FIG. 3). In further embodiments, the testing apparatus 1322 may be separate from a computer and/or EMI console. In still other embodiments, a testing apparatus 1322 may be used in connection with a computer and/or EMI console. In some embodiments, a fault indicator array (e.g., fault indicator arrays 1156, 1256 of FIGS. 11 and 12) may be incorporated into and/or used in connection with a computer and/or EMI console. In further embodiments, a fault indicator array may be incorporated into and/or used in connection with a testing apparatus as described herein.

Figure 14:
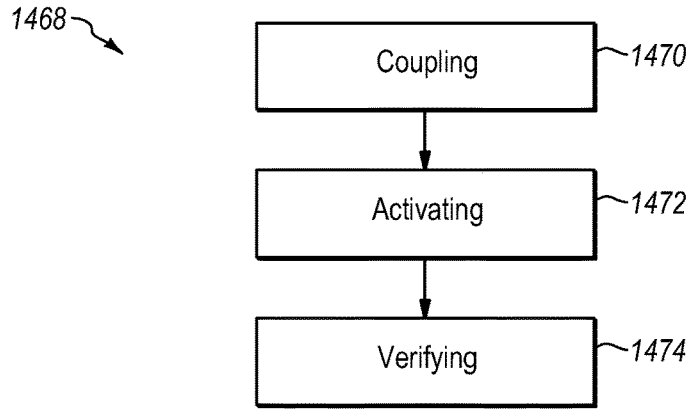
FIG. 14 depicts a method of testing an inspection unit according to one or more embodiments disclosed herein.
Figure 15:
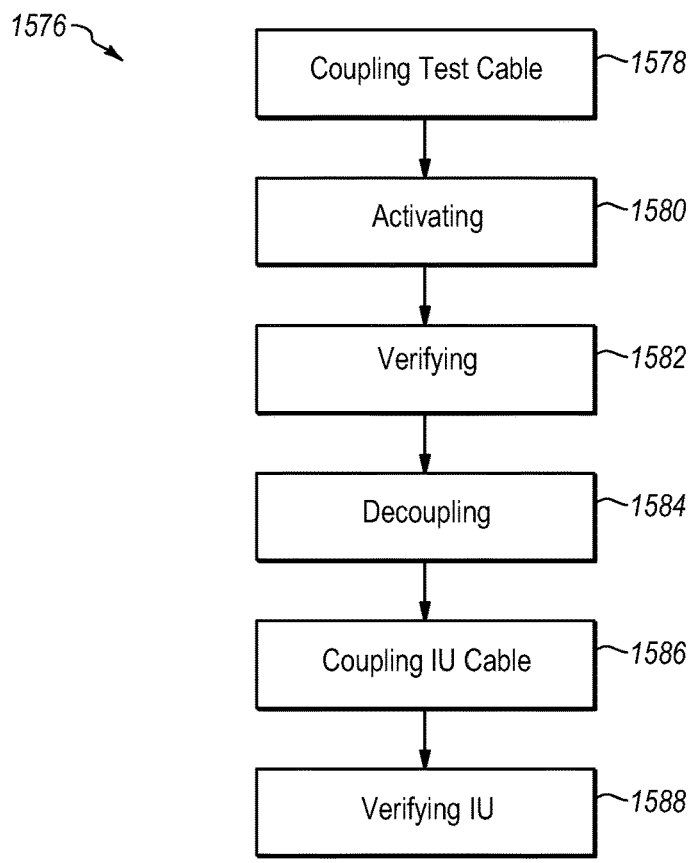
FIG. 15 depicts a method of testing an inspection unit and an inspection unit cable according to one or more embodiments disclosed herein.

FIGS. 14 and 15 are example workflows of methods for testing inspection equipment. FIG. 14 illustrates a method 1468 for testing an inspection unit. Testing an inspection unit may include coupling 1470 the testing apparatus to the component or components of the inspection unit to be tested, activating 1472 the testing apparatus, and verifying 1474 the performance of the component to be tested. Verifying 1474 the performance of the component to be tested may include visually observing the performance or measuring the performance using another device. For example, the performance of a motor may be verified by visually confirming the movement and/or operation of the motor. In another example, the performance of an electromagnetic coil may be verified by measuring the presence of a magnetic field by a field detector. In yet another example, the performance of a signal cable may be verified by observing the response of a fault indicator and/or fault indicator array.

In another embodiment, depicted in FIG. 15, a method 1576 for testing a component of an inspection unit may include coupling 1578 a test cable of a testing apparatus to the component of the inspection unit. The method 1576 may also include activating 1580 the testing apparatus and verifying 1582 the performance of the component of the inspection unit. The test cable may be decoupled 1584, and after decoupling the test cable, the inspection unit may be coupled 1586 to the component of the inspection unit and to the testing apparatus. Performance of the component of the inspection unit may be verified 1588. In at least one embodiment, verifying the performance of the component of the inspection unit without using the inspection unit cable before verifying the performance of the component of the inspection unit using the inspection unit cable may reduce variables in the testing method 1576. In another embodiment, verifying the performance of the component of the inspection unit with a previously inspected inspection unit cable before verifying the performance of the component of the inspection unit may reduce variables in the testing method 1576. For example, if verifying the performance of a motor using an inspection unit cable (which may be a motor cable, in such a situation), a failure of the motor to respond may be due to a faulty motor and/or a faulty motor cable. If verifying the performance of a motor using a test cable affixed to the testing apparatus, a failure of the motor to respond may be determined to be due to a faulty motor. If a test is first run on the motor cable, a determination can also be made if the motor cable is faulty prior to running a test on the motor. In at least one embodiment, testing a faulty component of an inspection unit using a testing apparatus in accordance with the present disclosure may prevent damage to an EMI Console and/or computer.

Figure 16:
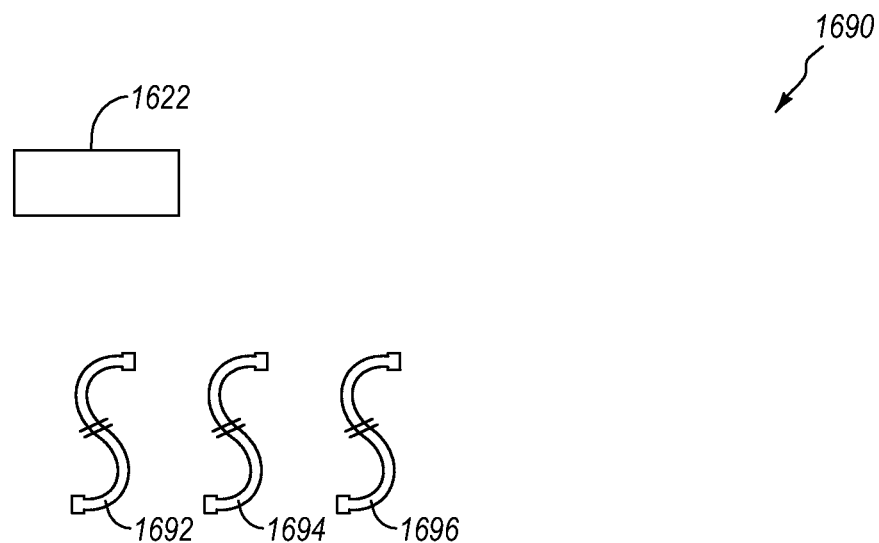
FIG. 16 depicts an equipment testing kit including replacement cables according to one or more embodiments disclosed herein.

FIG. 16 depicts a kit 1690 for testing inspection equipment. A kit 1690 may include a testing apparatus 1622 in accordance with the present disclosure and one or more inspection unit cables (e.g., replacement inspection unit cables). In some embodiments, the kit 1622 may include a motor cable 1692, an electromagnetic coil cable 1694, a signal cable 1696, any other appropriate replacement cable, or combinations thereof.

Figure 17:
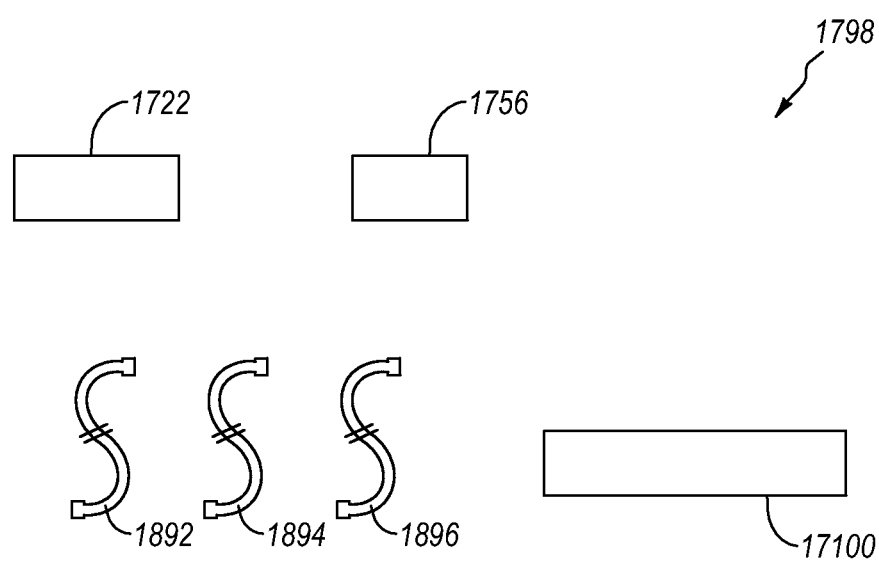
FIG. 17 depicts an equipment testing kit including additional replacement components according to one or more embodiments disclosed herein.

FIG. 17 depicts another embodiment of a kit 1798 for testing inspection equipment. A kit 1798 may include a testing apparatus 1722 in accordance with the present disclosure, a signal cable continuity tester 1756 in accordance with the present disclosure, and potentially one or more replacement components or parts. In some embodiments, the kit 1722 may include a replacement motor cable 1792, a replacement electromagnetic coil cable 1794, a replacement signal cable 1796, any other appropriate replacement cable, a replacement EMI Console 17100, or combinations thereof.

Figure 18:
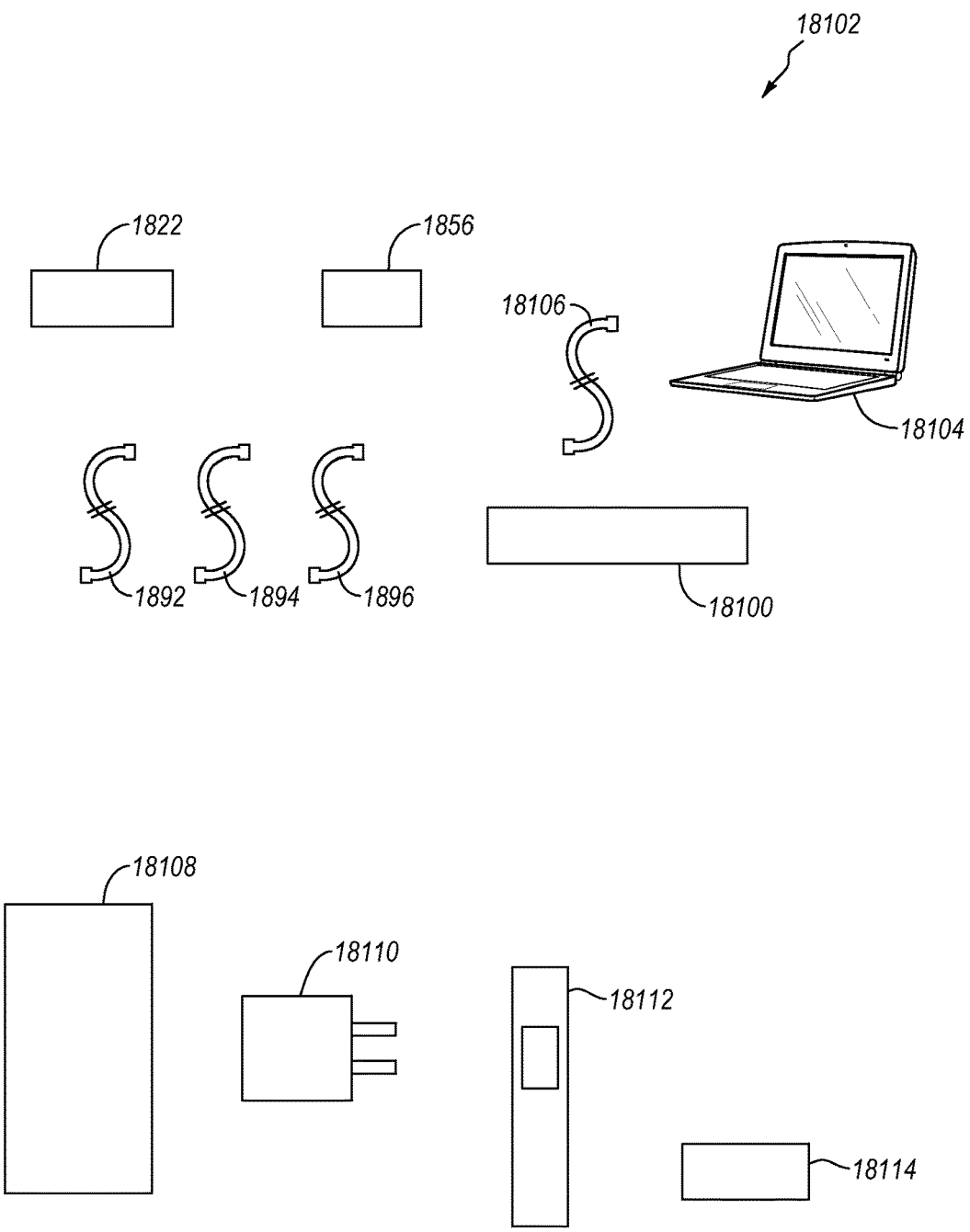
FIG. 18 depicts an equipment testing kit including replacement inspection unit components according to one or more embodiments disclosed herein.

FIG. 18 depicts another embodiment of a kit 18102 for testing inspection equipment. A kit 18102 may include a testing apparatus 1822 in accordance with the present disclosure, a signal cable continuity tester 1856 in accordance with the present disclosure, and replacement parts. In some embodiments, the kit 18102 may include a replacement motor cable 1892, a replacement electromagnetic coil cable 1894, a replacement signal cable 1896, any other appropriate replacement cable, a replacement EMI Console 18100, a replacement electromagnetic coil 18108, a replacement detection head 18110, a replacement buggy 18112, a replacement motor 18114, additional parts, or combinations thereof.

Figure 19:
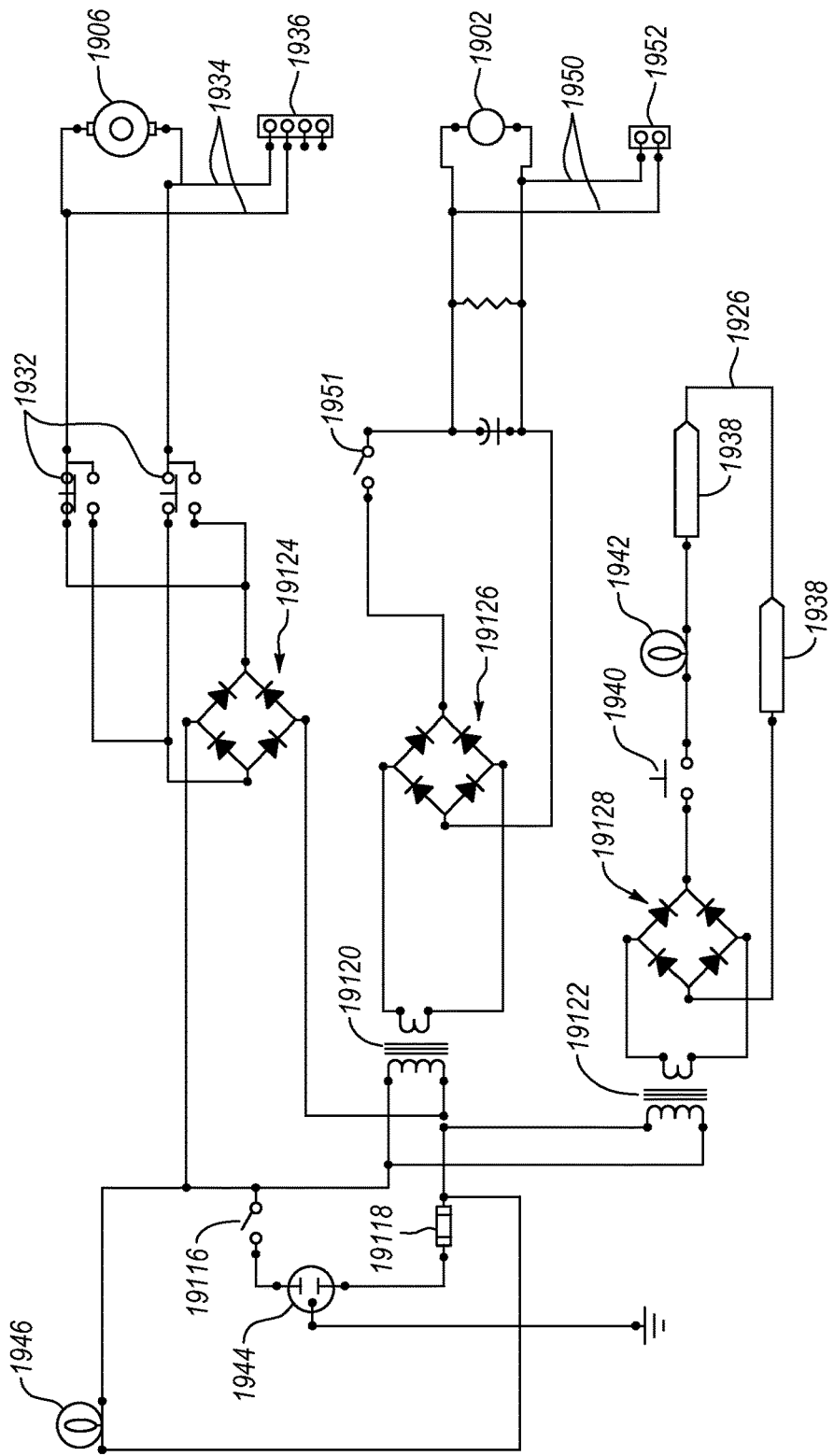
FIG. 19 is a circuit diagram of a testing apparatus according to one or more embodiments disclosed herein.

FIG. 19 is a circuit diagram depicting some embodiments of a testing apparatus in accordance with the present disclosure. The components to be tested are visualized on the right side of the circuit diagram. A power supply 1944 provides electrical energy to the apparatus. In some embodiments, the power supply 1944 may provide an about 120 Volt alternative current electrical signal. When a power switch 19116 is closed, electrical communication may be established with the testing apparatus and electrical energy may be provided to the various elements of the testing apparatus and the components to be tested. When the power switch 19116 is closed, a power indicator 1946 may illuminate, indicating there is electrical energy available from the power supply 1944. A circuit protection device 19118, such as a fuse, a circuit breaker, or other circuit termination mechanism, may be in electrical series between the power supply 1944 and the remainder of the testing apparatus to protect the testing apparatus from high voltages or amperages. In some embodiments, the circuit protection device 19118 may include a fuse rated at about 5 Amperes. In another embodiment, the circuit protection device 19118 may include a circuit breaker configured to break the circuit at about 5 Amperes.

The power supply 1944 may supply power to a first bridge 19124 that rectifies the incoming electrical energy and ensures a direct current signal is provided to the first switch 1932. The first switch 1932 may be a three-position reverse switch and is depicted in FIG. 19 in a forward closed position, thereby providing electrical communication between the first bridge 19124 and a motor 1906. The first switch 1932 may also have a reverse closed position, providing electrical communication between the first bridge 19124 and the motor 1906 in a reverse polarity.

The power supply 1944 may also supply power to a first transformer 19120. The first transformer 19120 may convert the electrical energy from the power supply 1944 into an electrical signal with a voltage and amperage suitable for a particular component of an inspection unit to be tested, such as an electromagnetic coil. In some embodiments, the first transformer 19120 may convert the incoming about 120 Volt alternating current to about 44 Volt and about 1 Ampere alternating current. The first transformer 19120 may then be in electrical communication with a second bridge 19126. The second bridge 19126 may be in electrical communication with a two-position gate switch 1951. When closed, the two-position gate switch 1951 may allow electrical communication between the second bridge 19126 and an electromagnetic coil 1902.

The power supply 1944 may also supply power to a second transformer 19122. The second transformer 19122 may convert the electrical energy from the power supply 1944 into an electrical signal with a voltage and amperage suitable for a particular component of an inspection unit to be tested, such as a signal cable. In some embodiments, the second transformer 19122 may convert the incoming about 120 Volt alternating current to about 6.3 Volt and about 0.3 Ampere alternating current. The second transformer 19122 may then be in electrical communication with a third bridge 19128. The second bridge 19128 may be in electrical communication with a pressure-activated gate switch 1940. When closed, the pressure-activated gate switch 1940 may allow electrical communication between the second bridge 19126 and a signal cable 1926. The signal cable is connection through test connections 1938 and, when the circuit is closed and electrical energy is provided, a fault indicator 1942 may indicate the condition of the signal cable 1926.

In the description herein, various relational terms are provided to facilitate an understanding of various aspects of some embodiments of the present disclosure. Relational terms such as "bottom," "below," "top," "above," "back," "front," "left," "right," "rear," "forward," "up," "down," "horizontal," "vertical," "clockwise," "counterclockwise," "upper," "lower," and the like, may be used to describe various components, including their operation and/or illustrated position relative to one or more other components. Relational terms do not indicate a particular orientation for each embodiment within the scope of the description or claims. Accordingly, relational descriptions are intended solely for convenience in facilitating reference to various components, but such relational aspects may be reversed, flipped, rotated, moved in space, placed in a diagonal orientation or position, placed horizontally or vertically, or similarly modified. Certain descriptions or designations of components as "first," "second," "third," and the like may also be used to differentiate between identical components or between components which are similar in use, structure, or operation. Such language is not intended to limit a component to a singular designation. As such, a component referenced in the specification as the "first" component may be the same or different than a component that is referenced in the claims as a "first" component.

Furthermore, while the description or claims may refer to "an additional" or "other" element, feature, aspect, component, or the like, it does not preclude there being a single element, or more than one, of the additional element. Where the claims or description refer to "a" or "an" element, such reference is not be construed that there is just one of that element, but is instead to be inclusive of other components and understood as "at least one" of the element. It is to be understood that where the specification states that a component, feature, structure, function, or characteristic "may," "might," "can," or "could" be included, that particular component, feature, structure, or characteristic is provided in some embodiments, but is optional for other embodiments of the present disclosure. The terms "couple," "coupled," "connect," "connection," "connected," "in connection with," and "connecting" refer to "in direct connection with," or "in connection with via one or more intermediate elements or members." Components that are "integral" or "integrally" formed include components made from the same piece of material, or sets of materials, such as by being commonly molded or cast from the same material, or commonly machined from the same piece of material stock. Components that are "integral" should also be understood to be "coupled" together.

Although various example embodiments have been described in detail herein, those skilled in the art will readily appreciate in view of the present disclosure that many modifications are possible in the example embodiments without materially departing from the present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features or elements from the various embodiments disclosed may be employed in combination with any other features or elements disclosed herein.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

While embodiments disclosed herein may be used in inspection services for drill pipes (including casing, liner, heavy weight drill pipe, drill collars, and the like) or other tubulars used in the oil, gas, or other hydrocarbon exploration or production environments, such environments are merely illustrative. Systems, tools, assemblies, methods, testing devices, and other components of the present disclosure, or which would be appreciated in view of the disclosure herein, may be used in other applications and environments. In other embodiments, testing devices or methods of testing inspection equipment may be used outside of a downhole environment, including in connection with systems in the automotive, aquatic, aerospace, hydroelectric, manufacturing, telecommunications industries.

The Abstract at the end of this disclosure is provided to allow the reader to quickly ascertain the general nature of some embodiments of the present disclosure. It is submitted with the understanding that it will not be used to interpret or limit the scope or meaning of the claims.

What is claimed is:

1. A testing apparatus for a drill pipe inspection equipment, comprising:
   a first test connector;
   a second test connector; and
   a fault indicator configured to indicate an operational condition of at least one element of the drill pipe inspection equipment when coupled to the first and second test connectors, the at least one element of the drill pipe inspection equipment configured to inspect a drill pipe for one or more of structural integrity of a tubular portion of the drill pipe, material composition of the drill pipe, material thickness of the drill pipe, corrosion of the drill pipe, or deformation of the drill pipe.

2. The testing apparatus of claim 1, the at least one element of the drill pipe inspection equipment including a cable, the fault indicator being configured to indicate the operational condition of the cable when coupled to the first and second test connectors, the cable being configured to provide one or more of data or power.

3. The testing apparatus of claim 2, the cable being a multi-wire cable, and the fault indicator configured to indicate an operational condition of each wire of the multi-wire cable.

4. The testing apparatus of claim 1, the fault indicator including a light.

5. The testing apparatus of claim 1, the fault indicator including an array.

6. The testing apparatus of claim 1, further including a switch configured to selectively allow electrical communication between the first test connector and the second test connector.

7. The testing apparatus of claim 6, the switch including a two-position switch.

8. The testing apparatus of claim 1, further comprising:
at least a third test connector configured to couple to an additional drill pipe inspection equipment.

9. The testing apparatus of claim 8, the additional drill pipe inspection equipment including at least one of a motor or a detection head.

10. A testing apparatus for a drill pipe inspection equipment, comprising:
a first test connector;
a second test connector;
a fault indicator configured to indicate an operational condition of at least one element of the drill pipe inspection equipment coupled to the first and second test connectors, the at least one element of drill pipe inspection equipment configured to inspect drill pipe for two or more of structural integrity of the drill pipe, material composition of the drill pipe, material thickness of the drill pipe, corrosion of the drill pipe, or deformation of the drill pipe of the drill pipe; and
a switch configured to selectively allow electrical communication between the first test connector and the second test connector, the switch including a three-position reverse switch.

11. A method for testing a drill pipe inspection equipment, comprising:
accessing the drill pipe inspection equipment configured to inspect a drill pipe, wherein the drill pipe inspection equipment includes:
a first test connection configured to selectively allow electrical communication therethrough;
a second test connection configured to selectively allow electrical communication therethrough; and
a third test connection including a third input configured to selectively allow electrical therethrough;
coupling a motor to the first test connection and selectively allowing electrical communication thereto;
with the motor coupled to the first test connection, testing a motor direction;
coupling at least one electromagnetic coil to the second test connection and allowing electrical communication thereto;
with the at least one electromagnetic coil coupled to the second test connection, testing an electromagnetic field of the at least one electromagnetic coil;
coupling a signal cable to the third test connection and allowing electrical communication thereto; and
with the signal cable coupled to the third test connection, testing a condition of multiple wires inside the signal cable.

12. The method of claim 11 further comprising verifying performance of the cable.

13. The method of claim 12, wherein verifying performance of the cable includes viewing a fault indicator of the drill pipe inspection equipment.

14. The method of claim 13, wherein viewing the fault indicator includes viewing a fault indicator array.

15. The method of claim 14, wherein the fault indicator array includes an array location corresponding to each wire of the cable.

16. The method of claim 15, wherein the fault indicator array includes more array locations than the cable includes wires.

17. The method of claim 11, each of the first, second, and third test connections including at least two connectors and a switch.

18. The method of claim 11, the third test connection including a 32-pin connector.

19. The method of claim 11, further comprising powering up the drill pipe inspection equipment.

* * * * *